Figure 1:
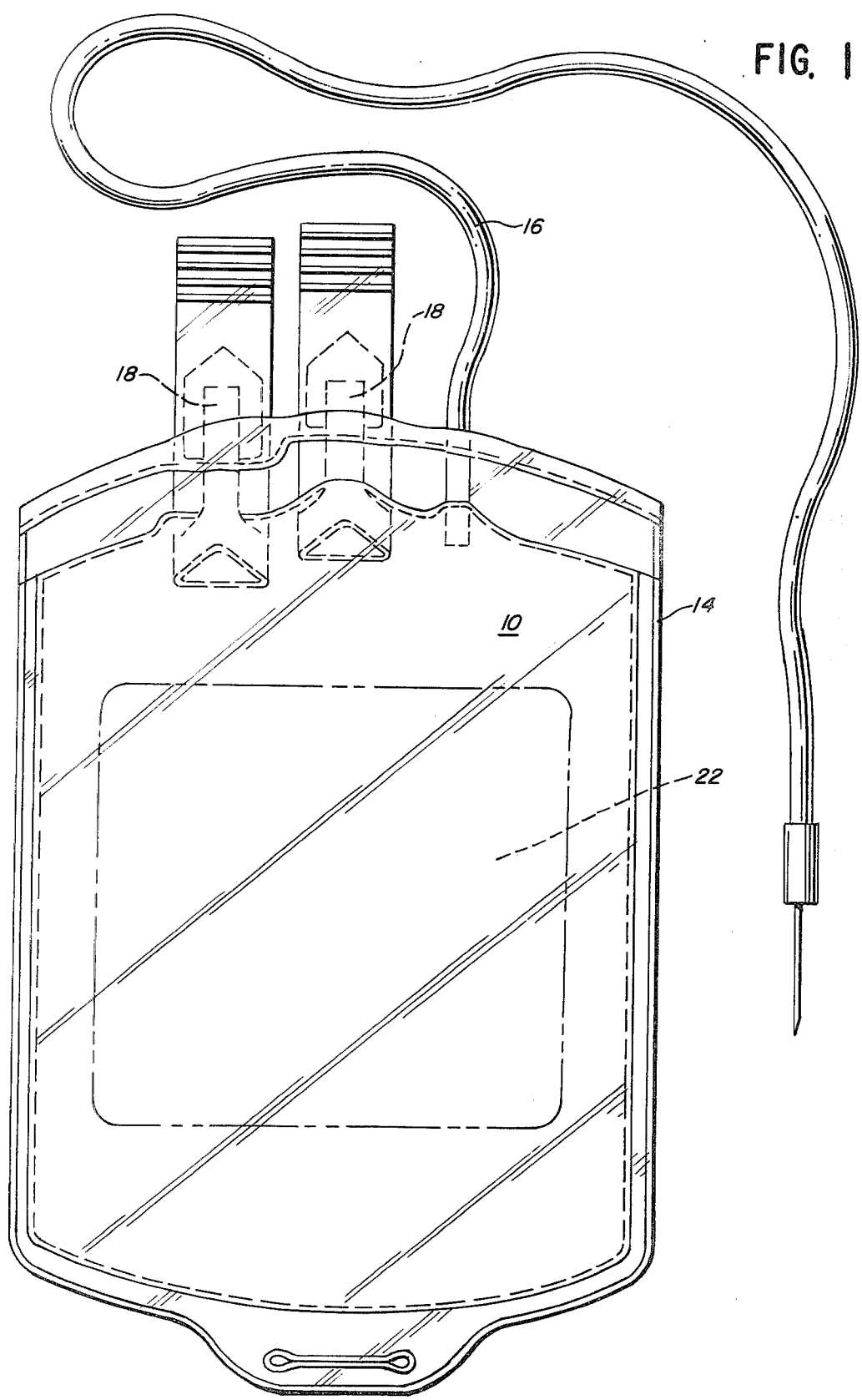

United States Patent [19]

Collins

[11] 4,301,800
[45] Nov. 24, 1981

[54] BLOOD BAGS HAVING AN INSERT MEMBER

[75] Inventor: Henry W. Collins, Deerfield, Ill.

[73] Assignee: Baxter Travenol Laboratories, Inc., Deerfield, Ill.

[21] Appl. No.: 151,447

[22] Filed: May 19, 1980

Related U.S. Application Data

[63] Continuation of Ser. No. 954,969, Oct. 26, 1978, abandoned.

[51] Int. Cl.$^3$ .............................................. A61M 5/00
[52] U.S. Cl. ........................... 128/272; 128/DIG. 24; 128/214 D
[58] Field of Search ............... 128/214 R, 214 D, 272, 128/DIG. 24, 130; 422/44

[56] References Cited

U.S. PATENT DOCUMENTS

| | | | |
|---|---|---|---|
| 3,064,647 | 11/1962 | Earl | 128/214 D |
| 3,186,961 | 6/1965 | Sears et al. | 260/30.4 |
| 3,279,996 | 10/1966 | Long et al. | 128/348 |
| 3,710,795 | 1/1973 | Higuchi et al. | 128/260 |
| 3,940,802 | 3/1976 | Sako et al. | 128/214 D |
| 3,977,404 | 8/1976 | Theeuwes | 128/260 |
| 4,082,509 | 4/1978 | Talcott | 128/214 D |
| 4,112,070 | 9/1978 | Harmening | 424/101 |

OTHER PUBLICATIONS

"Reduction of Haemolysis Perfusion by Collection and Storage of Blood in Plastic Bags", *The Lancet*, Snow et al., Jul. 16, 1960, p. 154.

*Primary Examiner*—Robert W. Michell
*Assistant Examiner*—T. J. Wallen
*Attorney, Agent, or Firm*—Paul C. Flattery; John A. Caruso; Garrettson Ellis

[57] ABSTRACT

A blood bag or other container which is made of a flexible, hemocompatible, sterilizable plastic material free of blood-extractable plasticizer. The blood bag contains an insert member which comprises a non-toxic, sterilizable plastic formulation which contains from 5 to 70 percent by weight of a blood-extractable plasticizer selected from the group consisting of the dioctylphthalates and dioctyladipates. Such a blood bag is capable of reducing the plasma hemoglobin in stored blood, when compared with similar blood bags without the insert member.

19 Claims, 1 Drawing Figure

BLOOD BAGS HAVING AN INSERT MEMBER

CROSS-REFERENCE TO RELATED APPLICATION

This application is a continuation of U.S. Application Ser. No. 954,969, filed Oct. 26, 1978, abandoned Aug. 22, 1980.

BACKGROUND OF THE INVENTION

Multiple blood bags are commercially available from the Fenwal Division of Baxter Travenol Laboratories, Inc. for collecting and processing blood under sterile conditions, to obtain various blood components that may be desired, for example, packed red cells, plasma, platelets, and cryoprecipitate.

The currently-available blood bags are made of a polyvinyl chloride formulation which includes, as an ester-type plasticizer, di-2-ethylhexylphthalate. Such a plasticizer is absolutely necessary for polyvinyl chloride formulations, since polyvinyl chloride itself is not a suitable flexible plastic material for use as a container. Such blood bags have served extremely well in the storage and processing of blood and blood components, exhibiting a high survival rate with a low plasma hemoglobin content after, for example, 21 days of storage.

Other chlorine-free plastic formulations have been tested as candidate blood bag materials as well, including flexible polyesters, polyolefins, and the like. Surprisingly, many of the materials tested, while giving indications of being good plastic materials for the manufacture of blood bags, have caused blood stored in containers made of such materials under the usual blood storage conditions to exhibit an undesirably high plasma hemoglobin content after, for example, 21 days of storage, indicating that the lysis rate of the red blood cells is high.

In accordance with this invention, it has been surprisingly found that the presence of certain ester-type plasticizers such as di-2-ethylhexylphthalate and di-2-ethylhexyladipate in various chlorine-free plastics which do not normally contain such plasticizers causes a significant lowering of the plasma hemoglobin content during long-term storage of blood in containers made of such plastic, when compared with containers made of similar plastic materials which are free of the ester-type plasticizers. This can be used to provide blood bags and other blood-contacting medical devices which are made out of chlorine-free plastic entities, having different advantages and properties as may be desired, but which nevertheless exhibit a similar desirably low blood hemolysis rate during long-term storage to that presently available in commercial polyvinyl chloride formulations.

DESCRIPTION OF THE INVENTION

In accordance with this invention, a blood bag or container may be provided which comprises a sealed container equipped with access tubing and sealed access ports, the container material being essentially free of blood-extractable plasticizers.

The blood bag or container contains an insert member, the insert member comprising a non-toxic, sterilizable plastic formulation which preferably contains from 5 to 70 percent by weight of a blood-extractable plasticizer selected from the group consisting of the dioctylphthalates and dioctyladipates.

It is specifically desirable for the concentration and distribution of plasticizer in the bag to be such that when the bag is filled with blood and stored on a long-term basis, the concentration of the blood-extractable plasticizer in the blood rises over 21 days to typically about 30 to 100 micrograms per ml., and preferably from about 50 to 80 micrograms per ml., in the blood. This takes place due to the extraction of the plasticizer from the plastic material in dissolved form into the blood.

It has been found to be difficult to dissolve the blood-extractable plasticizers used herein in bulk in the blood. It is found that a greater beneficial effect is provided by placing the extractable plasticizer in the plastic material of the blood bag for extraction by the blood during the storage.

This present invention permits the use of bag or container materials which are free of blood extractable plasticizers, without encountering significant increases in the plasma hemoglobin on storage of blood, as has been found with many otherwise desirable blood bag materials.

The plastic insert of this invention may be a sheet of plastic, plastic beads, or the like and may be positioned within the blood bag or container. The insert member contains the blood-extractable plasticizer for slow release to the interior of the bag or container.

Another advantage of the invention of this application is that rigid containers as well as bags may also be improved in their blood-storing capabilities by the addition of the insert member of this invention.

Preferably, the blood-extractable plasticizer used herein may be a branched octylphthalate, and particularly, di-2-ethylhexylphthalate.

In the plastic insert of this invention, the concentration of plasticizer may be up to about 70 percent if desired, although generally a concentration of about 15 to 50 percent of plasticizer is used. Since the insert is usually not a structural element, it does not have to have a high tensile strength.

The use of the above described blood bag or other container can result in a substantial reduction in plasma hemoglobin produced by blood stored under normal conditions for 21 days therein, when compared with blood in a corresponding, extractable plasticizer-free bag, stored under equivalent conditions.

The materials used in this invention may optionally be a polyester material containing the extractable plasticizer in the desired quantity. The polyester material may be made in accordance with the teachings of U.S. Pat. No. 4,045,431.

It may be desirable to incorporate the blood bag of this invention into a multiple bag system containing a plurality of blood bags connected by tubing, in which the additional blood bags may be of similar or different construction from the bag of this invention.

Alternatively, the compositions of this invention, and the resulting bags and medical tubing and similar devices made therefrom, may comprise other halogen-free plastic materials, free of blood-extractable plasticizers such as di-2-ethylhexylphthalate. Candidate polymer materials for this purpose include non-toxic polyurethanes, polyamide materials such as nylon, polycarbonates, polysulfones, polyacrylates, polyvinylacetate and copolymers thereof with other vinyl polymer materials such as ethylene, polyacrylates, (particularly those of a hydrophilic nature such as hydroxylated polyacrylates), and other similar materials.

Referring to the drawings, FIG. 1 is a plan view of a blood bag made in accordance with this invention.

Blood bag 10 may be made of conventional construction, including a pair of plastic sheets sealed at periphery 14 and containing a blood collection tube 16 (which may also be made of the composition of this invention) having the usual donor needle, and a pair of sealed access ports 18.

Bag 10 is made of a transparent, flexible, sterilizable and preferably autoclavable material which is generally free of blood-extractable plasticizer such as a dioctylphthalate or a dioctyladipate. Specifically, the plastic material of bag 10 may be the polyester formulation described above. Such blood bags, while exhibiting many good qualities, provide an undesirably high plasma hemoglobin content of blood stored under normal conditions for 21 days, in the absence of the insert of this invention.

As shown, plastic insert 22 may be placed within the bag 10. Insert 22 may be made of a similar material to the bag 10, or a different plastic material which is compatible with the desired blood-extractable plasticizer used herein. Accordingly, the material of bag 10 may be relatively free of the desired blood-extractable plasticizer, but insert 22 within the bag may carry any desired amount of the plasticizer, for example, 15 to 70 percent by weight, to provide extractable plasticizer to the blood which is placed in the bag 10. The result of this will be to cause bag 10 to exhibit a relatively reduced plasma hemoglobin content upon storage, when compared with a similar bag without insert 22.

Insert 22 may be a single sheet, or a plurality of plastic beads, or any other convenient structure. For example, in this particular alternate instance, blood bag 10 may be made out of a flexible, collapsible plastic material which is generally free of blood-extractable plasticizers. Specific plastic materials with which the blood bag may be made in this instance includes the polymers listed above, plus polyolefins such as polyethylene, polypropylene, or polyolefin block copolymer formulations as specifically described in U.S. Patent Application Ser. No. 819,924, filed July 28, 1977 now U.S. Pat. No. 4,140,162.

Insert 22, on the other hand, may be made of a blood-compatible plastic material including any of the above-listed polymers, for example, a blood-compatible polyvinylchloride formulation which may contain preferably up to about 50 percent di-2-ethylhexylphthalate or di-2-ethylhexyladipate, to be extracted into the blood over the storage period. If desired, higher concentrations than 50 percent of the extractable plasticizer may be placed in insert 22, since there is no need for insert 22 to exhibit a high tensile strength, as would be necessary if it were part of the bag wall itself.

Bag 10 may contain an appropriate blood preservative 30 such as ACD or CPD solution, as is conventional for storage of the blood. During storage, the presence of the plasticizer effectively suppresses the amount of plasma hemoglobin which is generated over a period of time, compared with blood stored in a bag made of an extractable plasticizer-free plastic formulation. Accordingly, the above described halogen-free plastic formulations may, for the first time, be formulated into blood bags and other medical devices for long-term contact with blood, while at the same time exhibiting an unexpectedly low red cell hemolysis rate, when compared with the corresponding plasticizer-free plastic formulations.

If desired, blood bag 10 may be equipped with a sterile connector device, for example that shown in U.S. Pat. No. 4,004,486, or any other sterile connector system, so that the bag may be connected together with other blood bags or sterile equipment without breaching the sterility of the system.

The above has been offered for illustrative purposes only and is not intended to limit the invention of this application, which is as defined in the claims below.

That which is claimed is:

1. A blood bag which comprises a flexible, translucent container equipped with access tubing and sealed access ports, said blood bag comprising: a flexible, hemocompatible, sterilizable plastic material, essentially free of blood-extractable plasticizer, said blood bag containing an insert member, said insert member comprising a non-toxic, sterilizable plastic formulation which contains from 5 to 70 percent by weight of a blood-extractable plasticizer selected from the group consisting of the dioctylphthalates and dioctyladipates.

2. The blood bag of claim 1 in which said plasticizer is dioctylphthalate.

3. The blood bag of claim 1 in which said plasticizer is di-2-ethylhexylphthalate.

4. The blood bag of claim 1 in which said plasticizer is di-2-ethylhexyladipate.

5. The blood bag of claim 1 in which said insert member is from 15 to 50 percent by weight of said plasticizer.

6. The blood bag of claim 5 in which said insert member is a plastic sheet.

7. The blood bag of claim 5 in which said insert member comprises a blood-compatible plasticized polyvinyl chloride formulation.

8. A blood container which comprises a hemo-compatible, sterilizable material, essentially free of blood-extractable plasticizer, said blood container containing an insert member, said insert member comprising a non-toxic, sterilizable plastic formulation which contains sufficient material selected from the group consisting of dioctylphthalates and dioctyladipates to cause blood stored in said blood bag for 21 days to exhibit a reduced plasma hemoglobin content when compared with blood stored in a comparable blood container free of said material.

9. The blood container of claim 8 in which said plasticizer is dioctylphthalate.

10. The blood container of claim 9 in which said plasticizer is di-2-ethylhexylphthalate.

11. A blood container which comprises a hemo-compatible, sterilizable material, essentially free of blood-extractable plasticizer, said blood container containing an insert member, said insert member comprising a non-toxic, sterilizable, plastic formulation which contains sufficient antihemolytic agent, capable of leaching from said plastic formulation, to cause blood stored in said blood bag for 21 days to exhibit a reduced plasma hemoglobin content when compared with blood stored in a comparable blood container free of said antihemolytic agent.

12. The method of storing blood which comprises placing said blood for a period of days into a flexible, hemocompatible, sterilizable plastic material, essentially free of blood-extractable plasticizer, said blood bag containing an insert member, said insert member comprising a non-toxic, sterilizable, plastic formulation which contains a blood extractable antihemolytic agent in sufficient quantity to cause blood stored in said blood bag for 21 days to exhibit a reduced plasma hemoglobin content when compared with blood stored in a comparable blood container free of said material.

13. The method of storing blood which comprises placing blood for a period of days in a blood bag made of a flexible, hemocompatible, sterilizable plastic material, essentially free of blood-extractable plasticizer, said blood bag containing an insert member, said insert member comprising a non-toxic, sterilizable plastic formulation which contains from five to 70 percent by weight of an antihemolytic material selected from the group consisting of the dioctylphthalates and dioctyladipates.

14. The method of claim 13 in which the material contained in said insert member is dioctylphthalate.

15. The method of claim 14 in which the material contained in said insert member is di-2-ethylhexylphthalate.

16. The method of claim 13 in which the material container in said insert member is di-2-ethylhexyladipate.

17. The method of claim 13 in which said insert member is from 15 to 50 percent by weight of said antihemolytic material.

18. The method of claim 13 in which said insert member is a plastic sheet.

19. The method of claim 13 in which said insert member comprises a blood-compatible, plasticized polyvinyl chloride formulation.

* * * * *